(12) United States Patent
Bowers et al.

(10) Patent No.: US 8,119,389 B2
(45) Date of Patent: Feb. 21, 2012

(54) RHODOCOCCUS ERYTHROPOLIS STRAIN

(75) Inventors: Nigel Ian Bowers, Yardley, PA (US); Paul M. Skonezny, Baldwinsville, NY (US); Gregory L. Stein, Mallory, NY (US); Thomas Franceschini, Cicero, NY (US); Shu-Jen Chiang, Manlius, NY (US); Wendy L. Anderson, Mexico, NY (US); Li You, Jamesville, NY (US); Zizhuo Xing, Syracuse, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 392 days.

(21) Appl. No.: 12/506,596

(22) Filed: Jul. 21, 2009

(65) Prior Publication Data
US 2009/0286303 A1  Nov. 19, 2009

Related U.S. Application Data

(62) Division of application No. 11/365,275, filed on Mar. 1, 2006, now Pat. No. 7,582,468.

(60) Provisional application No. 60/684,300, filed on May 25, 2005.

(51) Int. Cl.
*C12N 1/20* (2006.01)
(52) U.S. Cl. ............... 435/252.3; 435/280; 435/155
(58) Field of Classification Search .......... None
See application file for complete search history.

(56) References Cited

U.S. PATENT DOCUMENTS

| | | | |
|---|---|---|---|
| 5,391,495 A | 2/1995 | Patel et al. | |
| 5,726,047 A | 3/1998 | Sugawa et al. | |
| 5,849,911 A | 12/1998 | Fassler et al. | |
| 6,344,572 B1 | 2/2002 | Maehara et al. | |
| 6,605,732 B1 | 8/2003 | Malik et al. | |
| 6,737,264 B1 | 5/2004 | Maehara et al. | |
| 6,764,545 B2 | 7/2004 | Suzuki et al. | |
| 6,765,100 B2 | 7/2004 | Onishi et al. | |
| 7,083,973 B2 | 8/2006 | Patel et al. | |

FOREIGN PATENT DOCUMENTS
WO    WO 02/14528 A1    2/2002

*Primary Examiner* — Irene Marx
(74) *Attorney, Agent, or Firm* — John F. Levis

(57) ABSTRACT

The present invention relates to a process for preparing (2R, 3S)-1-halo-2-hydroxy-3-(protected)amino-4-substituted butane comprising contacting a mutagenized *Rhodococcus erythropolis* having ATCC deposit no. PTA-6648 with (3S)-1-halo-2-oxo-3-(protected)amino-4-substituted butane substrate. The present invention also relates to a process comprising mixing (2R,3S)-1-halo-2-hydroxy-3-(protected)amino-4-substituted butane with at least one base in the presence of at least one solvent to produce a reaction mixture containing (2R,3S)-1,2-epoxy-3-(protected)amino-4-substituted butane. The present invention further relates to a process comprising crystallizing the (2R,3S)-1,2-epoxy-3-(protected)amino-4-substituted butane out of the reaction mixture by concurrently adding water and the reaction mixture together. The present invention is also directed to a mutagenized *Rhodococcus erythropolis* having ATCC deposit no. PTA-6648.

1 Claim, No Drawings

RHODOCOCCUS ERYTHROPOLIS STRAIN

CROSS-REFERENCE TO RELATED APPLICATION

This divisional application claims the benefit of U.S. Ser. No. 11/365,275 filed Mar. 1, 2006, now allowed, which in turn claims the benefit of U.S. Provisional Application No. 60/684,300, filed May 25, 2005.

FIELD OF THE INVENTION

The present invention relates to a process for preparing (2R,3S)-1,2-epoxy-3-(protected)amino-4-substituted butane and intermediates thereof. More specifically, the invention relates to using a mutagenized *Rhodococcus erythropolis* strain having ATCC deposit No. PTA-6648 to microbiologically reduce (3S)-1-halo-2-oxy-3-(protected)amino-4-substituted butane to (2R,3S)-1-halo-2-hydroxy-3-(protected)amino-4-substituted butane. This invention further relates to converting (2R,3S)-1-halo-2-hydroxy-3-(protected)amino-4-substituted butane to (2R,3S)-1,2-epoxy-3-(protected)amino-4-substituted butane, and isolating (2R,3S)-1,2-epoxy-3-(protected)amino-4-substituted butane crystals.

BACKGROUND OF THE INVENTION 1-halo-2-hydroxy-3-(protected)amino-4-substituted butanes represented by the following general formula:

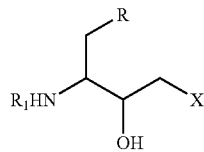
(1)

wherein X is a halogen, R is selected from alkyl, substituted alkyl, cycloalkyl, substituted cycloalkyl, aryl, and substituted aryl, and $R_1$ represents an amino-protecting group are useful in producing 1,2-epoxy-3-(protected)amino-4-substituted butane derivatives represented by the following general formula:

(2)

wherein R and $R_1$ are as defined above. The 1-halo-2-hydroxy-3-(protected)amino-4-substituted butanes of formula 1 can be prepared by microbiologically reducing a (3S)-1-halo-2-oxo-3-(protected)amino-4-substituted butane substrate having the following general formula:

(3)

wherein X, R, and $R_1$ are as defined above.

The 1,2-epoxy-3-(protected)amino-4-substituted butane derivatives of formula (2) may be used to produce various HIV protease, ACE, and renin inhibitors. The various HIV protease inhibitors that may be produced with the formula (2) intermediate include but are not limited to, for example, the HIV protease inhibitors disclosed in U.S. Pat. No. 5,849,911 at column 2, line 13 to column 12, line 59, wherein said disclosure is hereby incorporated herein by reference. The typical HIV protease inhibitor that may be produced with the formula (2) intermediate includes but is not limited to, for example, the [3S-(3R*,8R*,9R*,12R*)]-3,12-Bis(1,1-dimethylethyl)-8-hydroxy-4,11-dioxo-9-(phenylmethyl)-6{[4-(2-pyridinyl)phenyl]methyl}-2,3,6,10,13-pentaazaretetradecanedioic acid dimethyl ester compound disclosed in U.S. Pat. No. 5,849,911.

The 1,2-epoxy-3-(protected)amino-4-substituted butane derivatives of formula (2) can be synthesized in accordance with, for example, the following reaction scheme (1):

Reaction Scheme 1

Formula 3 substrate → microbial reduction → Formula 4 → Treatment with Base → Formula 6

Formula 5 → Treatment with Base → Formula 7

Formula 8 wherein X, R and $R_1$ of each of the Formulas 4-8 are as defined above. In accordance with reaction scheme (1), microbially reducing the formula 3 substrate to desired (2R,3S)-1-halo-2-hydroxy-3-(protected)amino-4-substituted butane diastereomer of formula 4 can also result in the production of undesired (2S,3S)-1-halo-2-hydroxy-3-(protected)amino-4-substituted butane diastereomer by-product of formula 5 and undesired des-halo alcohol (3S)-2-hydroxy-3-(protected)amino-4-substituted butane impurity of formula 8. The desired (2R,3S)-1-halo-2-hydroxy-3-(protected)amino-4-substituted butane diastereomer of formula 4 is subsequently treated with base and epoxidized to desired (2R,3S)-1,2-epoxy-3-(protected)amino-4-substituted butane of formula 6. The undesired (2S,3S)-1-halo-2-hydroxy-3-(protected)amino-4-substituted butane diastereomer by-product of formula 5, however, is upon being treated with base epoxidized to undesired (2S,3S)-1,2-epoxy-3-(protected)amino-4-substituted butane of formula 7.

SUMMARY OF THE INVENTION

The present invention relates to a process comprising preparing (2R,3S)-1-halo-2-hydroxy-3-(protected)amino-4-substituted butane of the formula:

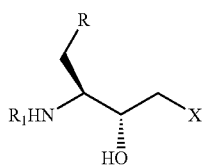

(4)

wherein X is a halogen, R is selected from alkyl, substituted alkyl, cycloalkyl, substituted cycloalkyl, aryl, and substituted aryl, and $R_1$ represents an amino-protecting group by contacting a mutagenized *Rhodococcus erythropolis* having ATCC deposit no. PTA-6648 with from 2.5 to about 6% w/v, based on substrate, (3S)-1-halo-2-oxo-3-(protected)amino-4-substituted butane substrate of the formula:

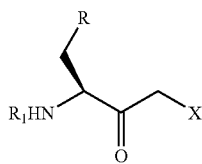

(3)

wherein X, R, and $R_1$ are as defined above.

The present invention further relates to i) producing a diastereomeric excess of formula (4) compound of at least about 95.1%; ii) biotransforming at least about 99.6% formula (3) substrate to formula (4) compound; iii) obtaining formula (4) compound at a diastereomeric purity of at least about 96%; and/or iv) producing less than about 0.6 area percentage of formula (8) des-halo alcohol impurity by contacting mutagenized *Rhodococcus erythropolis* having ATCC deposit no. PTA-6648 with formula (3) substrate in the presence of about 2 to about 6% (w/v) glycerol.

The present invention also relates to a process comprising utilizing centrifugation to separate the (2R,3S)-1-halo-2-hydroxy-3-(protected)amino-4-substituted butane of formula (4) from at least one impurity.

The present invention even further relates to a process comprising mixing the (2R,3S)-1-halo-2-hydroxy-3-(protected)amino-4-substituted butane of formula (4) with at least one base in the presence of at least one solvent selected from a polar organic solvent and a polar organic solvent and water to produce a reaction mixture comprising (2R,3S)-1,2-epoxy-3-(protected)amino-4-substituted butane of the formula

(6)

wherein R is selected from alkyl, substituted alkyl, cycloalkyl, substituted cycloalkyl, aryl, and substituted aryl and $R_1$ represents an amino-protecting group.

The present invention also relates to a process comprising crystallizing the formula (6) compound out of the reaction mixture by mixing the (2R,3S)-1-halo-2-hydroxy-3-(protected)amino-4-substituted butane of formula (4) with at least one base in the presence of at least one solvent selected from a polar organic solvent and a polar organic solvent and water by concurrently adding water and the reaction mixture together.

The present invention further relates to a mutagenized *Rhodococcus erythropolis* having ATCC deposit no. PTA-6648.

DETAILED DESCRIPTION OF THE INVENTION

The features and advantages of the present invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Unless specifically stated otherwise herein, references made in the singular may also include the plural. For example, "a" and "an" may refer to either one, or one or more.

All numbers expressing quantities of ingredients, properties such as molecular weight, reaction conditions, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

It is to be understood that each of the variously stated ranges is intended to be continuous so as to include each numerical parameter between the stated minimum and maximum value of each range. It is to be further understood that, while not intending to limit the applicability of the doctrine of equivalents to the scope of the claims, each numerical parameter should at least be construed in a manner consistent with the reported number of significant digits for each numerical parameter and by applying ordinary rounding techniques. It is to be even further understood that, while not intending to limit the applicability of the doctrine of equivalents to the scope of the claims, even though a number may be contained within a numerical range wherein at least one of the minimum and maximum numbers of the range is or is not preceded by the word "about", each numerical value contained within the range may or may not be preceded by the word "about". For Example, a range of about 1 to about 10 includes about 1, about 2, 2, about 3, 3, about 4, 4, about 5, 5, about 6, 6, about 7, 7, about 8, 8, about 9, 9, and about 10; a range of about 1.1 to about 3.2 includes about 1.1, about 1.2, 1.2, about 1.3, 1.3, about 1.4, 1.4, about 1.5, 1.5, about 1.6, 1.6, about 1.7, 1.7, about 1.8, 1.8, about 1.9, 1.9, about 2.0, 2.0, about 2.1, 2.1, about 2.2, 2.2, about 2.3, 2.3, about 2.4, 2.4, about 2.5, 2.5, about 2.6, 2.6, about 2.7, 2.7, about 2.8, 2.8, about 2.9, 2.9, about 3.0, 3.0, about 3.1, 3.1, and about 3.2; and a range of about 1 to 4 includes about 1, 2, about 2, 3, about 3, and 4.

Further, when an amount, concentration, or other value or parameter is given as a list of upper values and lower values, such listings are intended to include all ranges formed by pairing any upper value with any lower value, regardless of whether ranges are separately disclosed.

The definitions set forth herein take precedence over definitions set forth in any patent, patent application, and/or patent application publication incorporated herein by reference.

The abbreviation "d.e." as used herein means "diastereomeric excess".

The term "alkyl" refers to a substituted straight- or branched-chain saturated hydrocarbon group having from 1 to 7 carbon atoms. Exemplary "alkyl" groups include but are not limited to, for example, methyl; ethyl; propyl; isopropyl; n-butyl; t-butyl; pentyl; hexyl; isohexyl; heptyl and 4,4-dimethylpentyl.

The term "lower alkyl" refers to an alkyl group that has from 1 to 4 carbon atoms. It is of import to note that although the term "lower alkyl" is encompassed within the definition of "alkyl", the usage of the term "lower alkyl" is not intended to limit the definition of the term "alkyl" either explicitly or implicitly to a substituted straight- or branched-chain saturated hydrocarbon group having from 5 to 7 carbon atoms. Exemplary lower alkyl groups include but are not limited to, for example, methyl; ethyl; propyl; isopropyl; n-butyl; t-butyl; and isobutyl.

The term "substituted alkyl" refers to an alkyl group substituted at any available and substitutable position with one to four substituents selected from, for example, H; halogen; trifluoromethyl (—CF$_3$); trifluoromethoxy (—OCF$_3$); hydroxyl (—OH); alkoxy; cycloalkoxy; heterocyclooxy; oxo (=O); alkanoyl; alkyl; aryl; substituted aryl; aryloxy; aralkyl; alkanoyloxy; amino (NH$_2$); alkylamino; arylamino; aralkylamino; cycloalkylamino; heterocycloamino; and/or disubstituted amino.

The term "halogen" or "halo" refers to chlorine, bromine, fluorine, and iodine.

The term "aryl" refers to monocyclic or bicyclic aromatic hydrocarbon rings having from 6 to 12 carbon atoms in the ring portion. Exemplary aryl groups include but are not limited to, for example, phenyl; naphthyl; biphenyl; and diphenyl groups.

The term "substituted aryl" refers to an aryl group substituted with at least one substituent, preferably 1 to 4 substituents, at any available and substitutable ring position, or where valence allows on any rings fused or attached thereto. The at least one substituent can, for example, be selected from H; alkyl; substituted alkyl; halo; trifluoromethyl (—CF$_3$); trifluoromethoxy (—OCF$_3$); hydroxyl (—OH); alkoxy; cycloalkoxy; heterocyclooxy; alkanoyl; alkanoyloxy; amino (NH$_2$); alkylamino; dialkylamino; aryl; aralkylamino; cycloalkylamino; heterocycloamino; alkanoylamino; thiol (—SH); alkylthio; cycloalkylthio; heterocyclothio; ureido; nitro (—NO$_2$); cyano (—C≡N); carboxy (—CO$_2$H); carboxyalkyl; carbamyl (—C(=O)NH$_2$); alkoxycarbonyl; alkylthiono; arylthiono; alkylsulfonyl; sulfonamido (—SO$_2$NH$_2$); and/or aryloxy. Any chosen substituent can be further substituted by at least one substituent selected from H; halo; hydroxyl (—OH); alkyl; alkoxy, aryl; substituted alkyl; and aralkyl. When an aryl is substituted, each ring of the aryl may be substituted.

The term "cycloalkyl' refers to a saturated or partially unsaturated non-aromatic cyclic hydrocarbon ring system. For example, a cycloalkyl group can contain 1 to 3 rings with 3 to 7 carbons per ring, which may further be fused with an unsaturated carbocyclic ring containing from 3 to 7 carbons. Exemplary "cycloalkyl" groups include but are not limited to, for example, cyclopropyl; cyclobutyl; cyclopentyl; cyclohexyl; cycloheptyl; cyclobutenyl, cyclopentenyl, and cyclohexenyl.

The term "substituted cycloalkyl" refers to a cycloalkyl substituted with at least one substituent, preferably 1 to 4 substituents, more preferably 1 to 2 substituents, at any available point of attachment on either the cycloalkyl ring, or where valence allows on any rings fused or attached thereto. Exemplary substituents include, but are not limited to, for example, substituted alkyl; and/or at least one substituent described above as an exemplary alkyl substituent in defining the term "substituted alkyl".

The terms "heterocyclo", "heterocycle", and "heterocyclic" refer to a fully saturated or unsaturated, aromatic or nonaromatic cyclic group that is, for example, a 4 to 7 membered monocyclic, 7 to 11 membered bicyclic, or 10 to 15 membered tricyclic ring system having at least one heteroatom in at least one carbon atom-containing ring. Each heteroatom containing ring of the heterocycle, heterocyclic, or heterocyclo may contain 1, 2, or 3 heteroatoms selected from N, O, and/or S, wherein the N and/or S may optionally be oxidized and/or the N optionally quaternized. The heterocycle, heterocyclic, or heterocyclo may be attached to the remainder of the molecule via any available heteroatom or carbon atom.

Exemplary monocyclic heterocyclic groups include but are not limited to, for example, pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl.

Exemplary bicyclic heterocyclic groups include but are not limited to, for example, 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, and thienothienyl.

Smaller heterocylos include but are not limited to, for example, epoxides and aziridines.

The terms "substituted heterocycle", "substituted heterocyclic", and "substituted heterocyclo" refer to a heterocycle, heterocyclic, and heterocyclo, respectively, substituted at any available point of attachment, or where valence allows on any rings fused or attached thereto, with a substituted alkyl and/or at least one substituent described above as an exemplary alkyl substituent in defining the term "substituted alkyl".

Definitions for the various other groups recited herein are as follows: alkoxy is —$OR^a$; cycloalkoxy is —$OR^b$; heterocyclooxy is —$OR^c$; alkanoyl is —$C(=O)R^a$; aryloxy is —OAr; alkanoyloxy is —$OC(=O)R^a$; alkylamino is —$NHR^a$; arylamino is —NHAr; aralkyl is —$R^a$Ar; aralkylamino is —$NHR^a$Ar; disubstituted amino is —$NR^dR^e$; dialkylamino is —$NR^aR^a$; cycloalkylamino —$NHR^b$; heterocycloamino —$NHR^c$; alkanoylamino is —$NHC(=O)R^a$; alkylthio is —$SR^a$; cycloalkylthio is —$SR^b$; heterocyclothio is —$SR^c$; ureido is

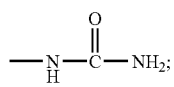

carboxyalkyl is —$R^aCO_2H$; alkoxycarbonyl is —$C(=O)OR^a$; aralkyloxycarbonyl is —$C(=O)OR^a$Ar; alkylthiono is —$S(=O)R^a$; arylthiono is —$S(=O)$Ar; and alkylsulfonyl is —$SO_{(q)}R^a$, wherein $R^a$ is alkyl or substituted alkyl; $R^b$ is cycloalkyl or substituted cycloalkyl; $R^c$ is heterocyclo or substituted heterocyclo; $R^d$ and $R^e$ are selected from alkyl, substituted alkyl, aryl, substituted aryl, and aralkyl; Ar is an aryl or substituted aryl; and q is 2 or 3.

Unless otherwise indicated, when the term "unsaturated" is used herein to refer to a ring or group, the ring or group may be fully unsaturated or partially unsaturated.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for aryl groups.

The term "amino-protecting group" refers to art-recognized moieties capable of attaching to an amino group so as to prevent the amino group from taking place in reactions occurring elsewhere on the molecule to which the amino group is attached. Acceptable amino-protecting groups, include but are not limited to, for example, amino-protecting groups described in "Protective Groups in Organic Synthesis", 2nd edition, John Wiley & Sons, 1991. The amino-protecting group may, for example, be a urethane type protective group (which is also referred to as a carbamate protective group) such as, for example, aralkyloxycarbonyl groups and alkoxycarbonyl groups. An amino-protecting group may, for example, be selected from benzyloxycarbonyl; methoxycarbonyl; and tert-butoxycarbonyl. Typically, the amino-protecting group is tert-butoxycarbonyl.

The abbreviation "ATCC" refers to the American Type Culture Collection, and/or the accession number assigned by the ATCC to the depository of the particular microorganism listed in conjunction with the abbreviation ATCC. The mutagenized *Rhodococcus erythropolis* having ATCC deposit no. 6648 as used herein refers to the strain *Rhodococcus erythropolis* P1B2 given patent Deposit Designation PTA-6648, and deposited on Mar. 29, 2005 with the ATCC at 10801 University Blvd., Manassas, Va. 20110-2209.

Fermentation and Biotransformation

The present invention relates to a process comprising preparing (2R,3S)-1-halo-2-hydroxy-3-(protected)amino-4-substituted butane of the formula:

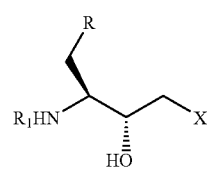

(4)

wherein X is a halogen, R is selected from alkyl, substituted alkyl, cycloalkyl, substituted cycloalkyl, aryl, and substituted aryl, and $R_1$ represents an amino-protecting group by contacting a mutagenized *Rhodococcus erythropolis* strain having ATCC deposit no. PTA-6648 with from 2.5 to about 6% w/v, based on substrate, (3S)-1-halo-2-oxo-3-(protected)amino-4-substituted butane substrate of the formula:

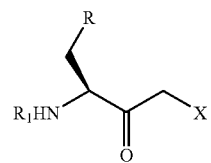

(3)

wherein X, R, and $R_1$ are as defined above.

The formula 3 substrate can be produced in accordance with methods readily known to a person of ordinary skill in the art. For example, the formula (3) substrate can be synthesized in accordance with the following reaction scheme 2:

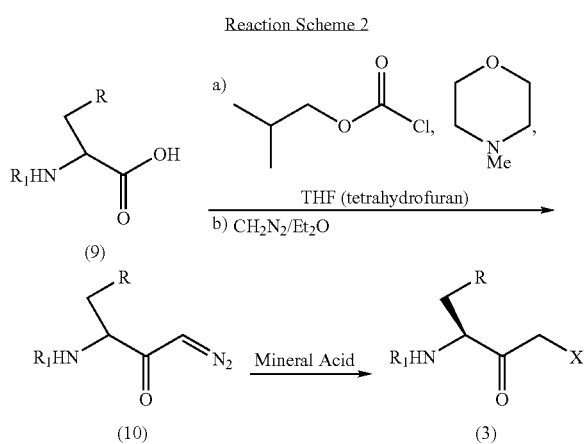

In accordance with reaction scheme 2, N-protected amino acid of the formula:

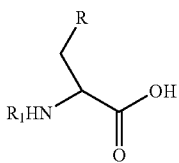

(9)

wherein R and $R_1$ are as defined above is treated with an alkyl formate, such as, for example, isobutyl chloroformate, and a tertiary amine, such as, for example, N-methyl morpholine, followed by the addition of a diazomethane/diethyl ether solution to give an N-protected amino acid diazoketone of the formula:

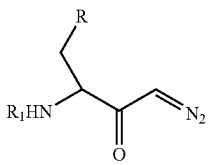

(10)

wherein R and $R_1$ are as defined above. The formula (10) compound can then be treated with a mineral acid, such as, for example, hydrochloric acid (HCl) or hydrobromic acid (HBr) to produce the desired formula (3) substrate.

The formula (3) substrate can also be synthesized by, for example, reacting a compound of the formula:

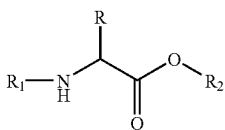

(11)

wherein R and $R_1$ are as defined above and $R_2$ is selected from alkyl, substituted alkyl, and benzyl, with at least 2 molar equivalents of a compound of the formula:

 Li—$CHX_1X_2$ (12)

wherein $X_1$ and $X_2$ are independently selected from chloro, bromo, iodo, and fluoro, provided at least one of $X_1$ or $X_2$ is bromo or iodo.

Moreover, if X of formula (3) is chlorine and R and $R_1$ are as defined above, the resulting (3S)-1-chloro-2-oxo-3-(protected)amino-4-substituted butane substrate can be synthesized by, for example, treating a compound of the formula:

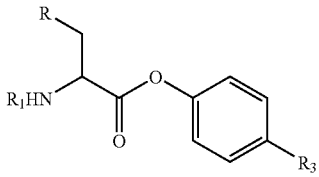

(13)

wherein R and $R_1$ are as defined above and $R_3$, which may be substituted on the phenyl ring in either the ortho or para position, is selected from hydrogen and nitrogen with a sulfur ylide containing compound of the formula:

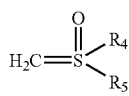

(14)

wherein $R_4$ and $R_5$ are independently selected from alkyl, substituted alkyl, aryl, and substituted aryl to produce an intermediate keto ylide compound of the formula:

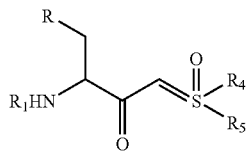

(15)

wherein R, $R_1$, $R_4$, and $R_5$ are as defined above. The formula (15) compound may then be reacted with a chloride source that may include but is not limited to, for example, a basic source of chloride, such as, for example, lithium chloride; and an organic acid, such as, for example, methanesulfonic acid.

In one embodiment, the formula (3) substrate is (S)-1-chloro-2-oxo-3-N-(tert-butoxycarbonyl)amino-4-phenylbutane. The (S)-1-chloro-2-oxo-3-N-(tert-butoxycarbonyl)amino-4-phenylbutane substrate can be produced in accordance with methods readily known to a person of ordinary skill in the art, including but not limited to, for example the general methods already set forth hereinabove for preparing formula (3) substrate.

In one embodiment, the formula (4) compound produced is (2R,3S)-1-chloro-2-hydroxy-3-N-(tert-butoxycarbonyl)amino-4-phenylbutane.

The formula (4) compound can be produced by contacting the formula (3) substrate with a mutagenized *Rhodococcus erythropolis* strain having ATCC deposit No. PTA-6648. The mutagenized *Rhodococcus erythropolis* strain having ATCC deposit No. PTA-6648 can produce a ketoreductase enzyme capable of biotransforming or enzymatically reducing formula (3) substrate to formula (4) compound.

In one embodiment, the ATCC PTA-6648 cells are contacted with from 2.5 to about 6% w/v, based on substrate, formula (3) substrate.

In another embodiment, the ATCC PTA-6648 cells are contacted with from about 4.5 to about 6% w/v, based on substrate, formula (3) substrate.

In yet another embodiment, the ATCC PTA-6648 cells are contacted with about 6% w/v, based on substrate, formula (3) substrate.

The ATCC PTA-6648 cells can be supplied, for example, as intact wet or dried cells, such as, for example, lyophilized, spray-dried, or heat-dried cells; or as treated cell material, such as, for example, ruptured cell or cell extract. The ATCC PTA-6648 cells can be grown to a high-cell density in accordance with any fermentation process readily known to a person of ordinary skill in the art including but not limited to, for example, a fed-batch fermentation process. The ATCC PTA-6648 cells can be grown in a container, such as, for example, a shake flask or fermentor tank.

The formula (3) substrate can be biotransformed to the formula (4) compound by being contacted with ATCC PTA-6648 cells in either a single-stage or in situ process, or a two-stage process.

The single-stage or in situ process involves concurrently biotransforming the formula (3) substrate to the formula (4) compound while at least some of the ATCC PTA-6648 cells are still fermenting. That is, the formula (3) substrate can be contacted with the ATCC PTA-6648 cells before all of the cells have finished fermenting. For example, the ATCC PTA-6648 cells can be grown in medium until sufficient cell growth is realized. Upon realizing sufficient ATCC PTA-6648 cell growth, the formula (3) substrate can be added directly to the ATCC PTA-6648 cell containing medium to form a reaction mixture slurry comprising ATCC PTA-6648 cells and formula (3) substrate. The formula (3) substrate can then be permitted to biotransform to the formula (4) compound for an effective amount of time to enable substantially all of the formula (3) substrate to be biotransformed to formula (4) compound.

The two-stage process involves first separately fermenting the ATCC PTA-6648 cells and then upon completing fermentation, contacting the formula (3) substrate with the fermented ATCC PTA-6648 cells. That is, the two-stage process involves first separately fermenting the cells and then using the separately fermented cells to biotransform the formula (3) substrate to the formula (4) compound. More specifically, in the two-stage process the ATCC PTA-6648 cells can be grown in medium until a predetermined level of ketoreductase enzymatic activity is exhibited. When the desired level of enzymatic activity is obtained, the grown cells can be separated from the medium and mixed with, for example, 0.1M sodium phosphate buffer to produce an ATCC PTA-6648 cell slurry having a pH of 7.4. The formula (3) substrate can then be added to the ATCC PTA-6648 cell slurry to form a reaction mixture slurry comprising ATCC PTA-6648 cells and formula (3) substrate. The formula (3) substrate can then be permitted to biotransform to the formula (4) compound for an effective amount of time to enable substantially all of the formula (3) substrate to be biotransformed to formula (4) compound.

The formula (3) substrate can be added as either a powder, or as a slurry in glycerol and water. Typically, however, the formula (3) substrate is added as a slurry in glycerol and water.

In one embodiment, the formula (3) substrate is contacted with the ATCC PTA-6648 cells in the presence of about 2 to about 6% (w/v) glycerol.

In another embodiment, glucose and glycerol carbon sources are added to the reaction mixture slurry throughout biotransformation to maintain about a 2.2% (w/v) concentration of glucose and about a 6% (w/v) concentration of glycerol.

The ATCC PTA-6648 cells can be grown in medium in accordance with any acceptable fermentation process known to a person of ordinary skill in the art including but not limited to, for example, a fed batch fermentation process.

A person of ordinary skill in the art is familiar with media acceptable for growing ATCC PTA-6648 cells including but not limited to, for example, media comprising broth; a carbon source; a nitrogen source; a trace element; and an antifoaming agent. The selected medium can have a pH, for example, of from about 6 to about 8, and typically of about 7.0. Typically, the medium utilized is aqueous.

The broth contained in the media includes but is not limited to, for example, tryptic soy broth (1.7% tryptone, 0.3% soytone, 0.5% sodium chloride, 0.25% glucose, 0.25% dipotassium phosphate, and pH 7.0); and F7 medium (2.2% glucose, 1% yeast extract, 1% malt extract, 0.1% peptone, and pH 7.0).

The carbon source typically contained in the medium includes but is not limited to, for example, sugar, such as, for example, maltose lactose, glucose, fructose, glycerol, sorbitol, sucrose, starch, and mannitol; and organic acids and their salts, such as, for example, sodium acetate and sodium citrate.

The nitrogen source typically contained in the medium includes but is not limited to, for example, N—Z amine A; corn steep liquor; soy bean meal; yeast extracts; molasses; baker's yeast; tryptone; nutrisoy; peptone; yeastamin; sodium nitrate; and ammonium sulfate.

The trace elements typically contained in the medium include but are not limited to, for example, phosphate; and a magnesium, manganese, calcium, cobalt, nickel, iron, sodium, and/or potassium salt.

The antifoaming agent typically contained in the medium includes, but is not limited to, for example, polypropylene glycol.

Commercially available media acceptable for growing ATCC PTA-6648 cells, include, but are not limited to, for example, alternative tryptic soy broth (available from Becton Dickinson Company, Sparks, Md.), which contains 1.8% soy protein; 0.2% yeast extract; 0.5% sodium chloride; 0.25% glucose; and 0.25% dipotassium phosphate.

The medium can, prior to being inoculated with ATCC PTA-6648 cells, be sterilized by, for example, being heated to a temperature of about 121° C. for about 30 minutes. The pH of the medium can then be adjusted, for example, to a pH of from about 6.5 to about 7.5, and typically to a pH of about 7.0. The pH can be adjusted with, for example, a base, such as, for example, ammonium hydroxide or an acid, such as, for example, phosphoric acid. The pH of the medium, however, can be adjusted in accordance with any method known to a person of ordinary skill in the art.

A person of ordinary skill in the art can use any method capable of detecting the point at which substantially all of the of the formula (3) substrate has been biotransformed to formula (4) compound, including but not limited to, for example, HPLC analysis. Typically, however, substantially all of the formula (3) substrate is biotransformed to formula (4) compound in about 4 to about 96 hours after the formula (3) substrate is contacted with the ATCC PTA-6648 cells, and even more typically in about 4 to about 48 hours.

The total amount of formula (3) substrate to be added to the ATCC PTA-6648 cells can be divided into four equal parts, wherein part one is added at about 0 hours, part two at about 4 hours, part 3 at about 8 hours, and part four at about 23 hours. For example, if a total of about 6% w/v formula (3) substrate is to be added to the cells, the about 6% w/v formula (3) substrate is divided into four equal parts of about 1.5% w/v each, wherein the first about 1.5% w/v part is added at about 0 hours, the second at about 4 hours, the third at about 8 hours, and the fourth at about 23 hours.

Alternatively, the formula (3) substrate can be continuously added to the ATCC PTA-6648 cells over a time period ranging from about 0 to about 24 hours. For example, if the formula (3) substrate is added in solid form, the formula (3) substrate can be added to the ATCC PTA-6648 cells via, for example, a solid screwfeeder that is set at constant delivery rate so as to enable the total amount of substrate being added to the ATCC PTA-6648 cells to be added within the desired timeframe. A person of ordinary skill in the art is familiar with similar processes that can be used in adding a slurry of formula (3) substrate in, for example, glycerol/water to the ATCC PTA-6648 cells.

In accordance with the single-stage or in situ processes, a person of ordinary skill in the art is generally familiar with methods available to determine the point at which sufficient ATCC PTA-6648 cell growth has been realized. For example, the ATCC PTA-6648 cells are generally sufficiently grown when the optical density at 600 nm of the culture is greater than 0.5.

In accordance with the two-stage process, the predetermined level of ketoreductase enzymatic activity is the point at which an optimal amount of ketoreductase enzyme has accumulated in the fermentation. An optimal amount of ketoreductase enzyme can typically be obtained after, for example, about 60 to about 96 hours of fermentation.

In the two stage process, the ATCC PTA-6648 cells can be separated from the medium with conventional separation techniques readily known to a person of ordinary skill in the art. Such conventional separation techniques, include but are not limited to, for example, membrane filtration and centrifugation.

The reaction mixture slurry containing the ATCC PTA-6648 cells and formula (3) substrate can also contain a buffering agent. Typical buffering agents include, but not limited to, for example, phosphate buffer; tris-hydrochloride buffer; bicine [N,N-bis(2-hydroxyethyl)glycine] buffer; tricin [N-tris(hydroxymethyl)methylglycine] buffer; and sodium acetate buffer.

In one embodiment, the formula (3) substrate is biotransformed to the formula (4) compound while the reaction mixture slurry is being aerated and agitated. The reaction mixture slurry can be aerated with, for example, from about 0.1 to about 10 volumes of air per volume of medium per minute (vvm), or, for example, with about 5 vvm. The reaction mixture slurry can be agitated, for example, at about 100 to about 2000 RPM, or, for example, at about 500 to about 1200 RPM.

In one embodiment, the reaction mixture slurry contains from about 1 to about 40 wt. %, based on wet cell weight, ATCC PTA-6648 cells.

In another embodiment, the reaction mixture slurry contains from about 20 to about 35 wt. %, based on wet cell weight, ATCC PTA-6648 cells.

In yet another embodiment, the reaction mixture slurry contains about 30 wt. %, based on wet cell weight, ATCC PTA-6648 cells.

Throughout the fermentation and biotransformation process the pH can be maintained, for example, at about 5.0 to about 9.0, or, for example, at about 6.0 to about 8.0; the temperature can be maintained, for example, at about 15° to about 38° C., or, for example, at about 25° to about 32° C.; and the pressure can be maintained, for example, at about atmospheric pressure.

In one embodiment, formula (3) substrate is contacted with ATCC PTA-6648 cells in the presence of about 2 to about 6% (w/v) glycerol to obtain formula (4) compound in a diastereomeric excess of at least about 95.1%.

In another embodiment, formula (3) substrate is contacted with ATCC PTA-6648 cells in the presence of about 2 to about 6% (w/v) glycerol to obtain formula (4) compound in a diastereomeric excess of at least about 95.6%.

In yet another embodiment, formula (3) substrate is contacted with ATCC PTA-6648 cells in the presence of about 2 to about 6% (w/v) glycerol to obtain formula (4) compound in a diastereomeric excess of at least about 96%.

In an even further embodiment, formula (3) substrate is contacted with ATCC PTA-6648 cells in the presence of about 2 to about 6% (w/v) glycerol to obtain formula (4) compound in a diastereomeric excess of at least about 97%.

In one embodiment, formula (3) substrate is contacted with ATCC PTA-6648 cells in the presence of about 2 to about 6% (w/v) glycerol to biotransform at least about 99.6% of formula (3) substrate to formula (4) compound.

In another embodiment, formula (3) substrate is contacted with ATCC PTA-6648 cells in the presence of about 2 to about 6% (w/v) glycerol to biotransform at least about 99.8% of formula (3) substrate to formula (4) compound.

In yet another embodiment, formula (3) substrate is contacted with ATCC PTA-6648 cells in the presence of about 2 to about 6% (w/v) glycerol to biotransform at least about 100% of formula (3) substrate to formula (4) compound.

In one embodiment, formula (3) substrate is contacted with ATCC PTA-6648 cells in the presence of about 2 to about 6% (w/v) glycerol to obtain formula (4) compound at a diastereomeric purity of at least about 96%.

In another embodiment, formula (3) substrate is contacted with ATCC PTA-6648 cells in the presence of about 2 to about 6% (w/v) glycerol to obtain formula (4) compound at a diastereomeric purity of at least about 97.5%.

In yet another embodiment, formula (3) substrate is contacted with ATCC PTA-6648 cells in the presence of about 2 to about 6% (w/v) glycerol to obtain formula (4) compound at a diastereomeric purity of at least about 97.9%

In an even further embodiment, formula (3) substrate is contacted with ATCC PTA-6648 cells in the presence of about 2 to about 6% (w/v) glycerol to obtain formula (4) compound at a diastereomeric purity of at least about 98.0%.

In yet an even further embodiment, formula (3) substrate is contacted with ATCC PTA-6648 cells in the presence of about 2 to about 6% (w/v) glycerol to obtain formula (4) compound at a diastereomeric purity of at least about 98.5%.

In one embodiment, less than about 0.6 area percentage des-halo alcohol (3S)-2-hydroxy-3-(protected)amino-4-substituted butane impurity of the formula:

(8)

wherein R and $R_1$ are as described above is produced when the formula (3) substrate is contacted with ATCC PTA-6648 cells in the presence of about 2 to about 6% (w/v) glycerol.

In another embodiment, less than about 0.5 area percentage of the formula 8 impurity is produced when the formula (3) substrate is contacted with ATCC PTA-6648 cells in the presence of about 2 to about 6% (w/v).

In yet another embodiment; less than about 0.4 area percentage of formula 8 impurity is produced when the formula (3) substrate is contacted with ATCC PTA-6648 cells in the presence of about 2 to about 6% (w/v).

In yet an even further embodiment; less than about 0.2 area percentage of formula 8 impurity is produced when the formula (3) substrate is contacted with ATCC PTA-6648 cells in the presence of about 2 to about 6% (w/v).

In one embodiment, the des-halo alcohol (3S)-2-hydroxy-3-(protected)amino-4-substituted butane impurity of formula 8 is tert-Butyl((1S)-1-benzyl-2-hydroxypropyl)carbamate.

Centrifugation

After substantially all of the formula (3) substrate has been biotransformed to formula (4) compound, the formula (4) compound can be separated from the reaction mixture slurry.

The formula (4) compound can be separated via a centrifugation process that involves first centrifuging the reaction mixture slurry to produce a) a heavy layer containing formula (4) compound and b) supernatant containing at least one impurity; and second extracting the formula 4 compound into an organic solvent.

In one embodiment, about 1% to about 35% formula (4) compound is contained in the heavy layer.

In another embodiment, about 10% to about 35% formula (4) compound is contained in the heavy layer.

In yet another embodiment, about 25% to about 35% formula (4) compound is contained in the heavy layer.

The at least one impurity that may be contained in the supernatant includes, but is not limited to, for example, the (2S,3S)-1-halo-2-hydroxy-3-(protected)amino-4-substituted butane diastereomer by-product of formula 5; at least about 70% ATCC PTA-6648 cells; propylene glycol; and salts.

The types of centrifuges that can be used in accordance with the present process include, but are not limited to, for example, a Beckman Coulter Allegra® 64R High-Speed Refrigerated Bench top Centrifuge (Beckman Coulter, Inc., Fullerton, Calif.) and a Westfalia Concurrent Extractor-Decanter (Westfalia Separator AG, Oelde, Germany).

In general, although the rate at which a reaction mixture slurry is centrifuged will depend on the type of centrifuge selected, the rate of centrifugation is typically optimized. For example, if a Beckman Coulter Allegra® 64R High-Speed Refrigerated Bench top Centrifuge is used, the reaction mixture slurry can be centrifuged at an optimized rate of about 3700 RPM for at least about 5 minute.

The optimized centrifugation rate of the Beckman Coulter Allegra® 64R High-Speed Refrigerated Bench top Centrifuge, however, can be used to calculate the optimal centrifugation rate of other centrifuges that may be used to centrifuge the reaction mixture slurry of the present invention. For example, Beckman Coulter Allegra® 64R High-Speed Refrigerated Bench top Centrifuge's optimized rate of 3700 RPMs can be converted to g-force, which is the force of gravity generated by the centrifuge, via the following equation:

$$g\text{-force} = \frac{r*(\text{rpm}*3.14/30)^2}{9.81};$$

r=radius of the rotor, i.e. radius in meters from spindle to sample bottom;
rpm=revolutions per minute; and
g is the acceleration due to gravity (9.81 m/sec2).

As the rotor radius of the Beckman Coulter Allegra® 64R High-Speed Refrigerated Bench top Centrifuge is 0.204 m and the optimized rate of centrifugation is 3700 RPMs, the g-force of the centrifuge is calculated to be about 3119×g. This calculated g-force can then be used in conjunction with the known radius of another centrifuge to calculate the approximate RPMs needed to meet the calculated g-force of the Beckman Coulter Allegra® 64R High-Speed Refrigerated Bench top Centrifuge.

In one embodiment, the reaction mixture slurry can, without being frozen, be chilled to a temperature of from about 0 to about 25° C. prior to being centrifuged.

In another embodiment, the reaction mixture slurry can, without being frozen, be chilled to a temperature of from about 0 to about 12° C. prior to being centrifuged.

In yet another embodiment, the reaction mixture slurry can, without being frozen, be chilled to a temperature of from about 1 to about 5° C. prior to being centrifuged.

In batch centrifugations, the size of the centrifuge bottle, volume of the reaction mixture slurry, temperature of the reaction mixture slurry, rpm of the centrifuge, and length of time the reaction mixture slurry is centrifuged can all affect the portion of heavy layer collected and the amount of impurity removed via supernatant. A person of ordinary skill in the art, however, generally knows how each of these parameters can be adjusted so as to optimize the amount of formula (4) crystals contained in the heavy layer while also optimizing the amount of impurity removed via supernatant.

In batch centrifugations, the collected heavy layer can be dewatered by being subjected to a second centrifugation step that enables a drier heavy layer to be separated from additional supernatant. The drier heavy layer can then be collected and the supernatant discarded. The centrifuges that can be used to dewater the harvested heavy layer include, but are not limited to, for example, the centrifuges already described hereinabove.

The drier heavy layer generally contains a) a dark colored top layer comprised of ATCC PTA-6648 cells and <1% by weight, based on the dark colored top layer, of formula 4 crystals; and b) a light colored bottom layer comprised of about 20 to about 35%, based on the light colored bottom layer, of formula (4) crystals, about 50 to about 60%, based on the light colored bottom layer, of water, and about 5 to about 30%, based on the light colored bottom layer, of residual ATCC PTA-6648 cells. The dark colored top layer can typically be separated from the light colored bottom layer by, for example, being manually removed with, for example, a spatula.

As a person of ordinary skill in the art may be aware, however, plant scale centrifuges are available that can eliminate the dewatering and manual separation steps of batch centrifugations. For example, a Westfalia Concurrent Extractor-Decanter (Westfalia Separator AG, Oelde, Germany) centrifuge can directly produce a satisfactorily dry heavy layer from the reaction mixture slurry. In addition, choosing the appropriate ring dam and optimizing the differential speed between the scroll and bowl of the Westfalia Extractor-Decanter centrifuge can enable the formula (4) crystals to be directly separated from the bulk of the ATCC PTA-6648 cells.

After being separated via centrifugation, the formula (4) compound can be extracted into an organic solvent by mixing the heavy layer or light colored bottom layer containing the formula (4) crystals with at least one organic solvent to form a first slurry. The first slurry can be formed, for example, by mixing the heavy layer or light colored bottom layer with the at least one organic solvent for at least about 5 minutes.

Exemplary organic solvents into which formula (4) compound can be extracted include, but are not limited to, for example, an aprotic polar organic solvent, such as, for example, acetone, methyl ethyl ketone, tetrahydrofuran, 1,4-dioxane, 1,3-dioxolane, 1,2-dimethoxyethane, diethylene glycol dimethyl ether, triethylene glycol dimethyl ether, tetraethylene glycol dimethyl ether, polyethylene glycol dimethyl ether, 1,2-diethoxyethane, diethylene glycol diethyl ether, triethylene glycol diethyl ether, tetra ethylene glycol diethyl ether, polyethylene glycol diethyl ether, acetonitrile, dimethylformamide, and dimethyl sulfoxide; a protic polar organic solvent, such as, for example, alcohols, such as, for example, methanol, ethanol, n-propanol, isopropanol, n-butanol, sec-butanol, isobutanol, and tert-butanol; and combinations thereof.

In one embodiment, the at least one organic solvent is a protic polar organic solvent.

In another embodiment, the protic polar organic solvent is isopropyl alcohol [IPA].

In order to facilitate downstream epoxidation and crystallization, it is of import to note that using a water immiscible solvent, such as, for example, ethyl acetate, MTBE, and/or heptane to extract formula (4) compound may involve 1) distilling off the water immiscible solvent, and 2) replacing the water immiscible solvent that was distilled off with a more water miscible solvent, such as, for example, acetone and/or IPA.

The heavy layer or light colored bottom layer can be mixed with from about 1 to about 10 volumes of the at least one organic solvent, and typically with from about 2 to about 4 volumes.

The first slurry can be prepared at a temperature ranging from about 0 to about 98° C., and typically at a temperature ranging from about 25 to about 30° C.

The first slurry can then be centrifuged to separate the slurry into 1) a lower phase containing residual ATCC PTA-6648 cells and residual formula (4) compound and 2) a rich aqueous organic solvent light phase containing formula (4) compound. The centrifuges that can be utilized include, but are not limited to, for example, the centrifuges already described hereinabove.

Optionally, the lower phase containing residual ATCC PTA-6648 cells and residual formula (4) compound can be further extracted with additional organic solvent and then separated via centrifugation. The centrifuges that can be utilized include, but are not limited to, for example, the centrifuges already described hereinabove.

In order to remove undesired process color, the first slurry may, prior to being centrifuged, optionally be mixed with a second slurry comprising at least one organic solvent and carbon to produce a third slurry. The second slurry can be prepared either by mixing the carbon with the at least one organic solvent, or if a water miscible organic solvent, such as, for example, IPA is used in preparing the first slurry, the carbon treatment can be performed concomitantly with extraction.

In one embodiment, the carbon is mixed with from about 0.1 to about 1 volume of the at least one organic solvent.

In another embodiment, the carbon is mixed with from about 0.2 to about 0.4 volume of the at least one organic solvent.

In one embodiment, about 1 to about 20% w/v, based on the heavy layer or the light colored bottom layer, of carbon is mixed with the at least one organic solvent.

In another embodiment, about 3 to about 6% w/v, based on the heavy layer or the light colored bottom layer, of carbon is mixed with the at least one organic solvent.

The carbon that can be utilized in preparing the second slurry includes but is not limited to, for example, Darco KB carbon.

The at least one organic solvent that can be utilized in preparing the second slurry includes, but is not limited to, for example, the organic solvents already described hereinabove.

The third slurry can be subsequently centrifuged to separate the slurry into a lower phase containing 1) at least one impurity including, but not limited to, for example, carbon, residual ATCC PTA-6648 cells, and residual formula (4) compound; and 2) a rich aqueous organic solvent light phase containing formula (4) compound. The centrifuges that can be utilized include, but are not limited to, for example, the centrifuges already described hereinabove.

Optionally, the lower phase containing at least one impurity can be further extracted with additional organic solvent and then separated via centrifugation. The centrifuges that can be utilized include, but are not limited to, for example, the centrifuges already described hereinabove. The organic solvent that can be utilized includes, but is not limited to, for example, the organic solvents already described hereinabove.

In accordance with the centrifugation process, the d.e. of formula (4) compound present in the rich aqueous organic solvent light phase is greater than the d.e. of formula (4) compound present in the post-biotransformation reaction mixture slurry.

In one embodiment, the d.e. of formula (4) compound present in the rich aqueous organic solvent light phase is increased over the amount present in the post-biotransformation reaction mixture slurry by about 0.5 to about 3.5%.

In another embodiment, the d.e. of formula (4) compound present in the rich aqueous organic solvent light phase is increased over the amount present in the post-biotransformation reaction mixture slurry by about 1.0 to about 3.5%.

In yet another embodiment, the d.e. of formula (4) compound present in the rich aqueous organic solvent light phase is increased over the amount present in the post-biotransformation reaction mixture slurry by about 1.5 to about 3.5%.

Epoxidation and Crystallization

The formula (4) compound can be epoxidized to (2R,3S)-1,2-epoxy-3-(protected)amino-4-substituted butane of formula (6) by mixing the formula (4) compound with at least one base in the presence of at least one solvent selected from a polar organic solvent and a polar organic solvent and water to produce a reaction mixture comprising formula (6) compound. The formula (4) compound can be epoxidized to the formula (6) compound either directly after being biotransformed from formula (3) substrate, or after being separated from the reaction mixture slurry. The formula (6) compound can be crystallized out of the reaction mixture by concurrently adding the reaction mixture and water together.

In one embodiment, the formula (6) compound is (2R,3S)-1,2-epoxy-3-N-(tert-butoxycarbonyl)amino-4-phenylbutane.

Exemplary bases that can be utilized in epoxidizing the formula (4) compound include, but are not limited to, for example, alkali metal hydroxides, such as, for example, lithium hydroxide, sodium hydroxide, and potassium hydroxide; alkali metal carbonates; alkaline earth metal hydroxides; alkaline metal carbonates; and combinations thereof.

In one embodiment, the at least one base is an alkali metal hydroxide.

In another embodiment, the at least one base is an alkaline earth metal hydroxide.

In yet another embodiment, the at least one base is an alkali metal hydroxide.

In an even further embodiment, the at least one base is potassium hydroxide.

The at least one base can be a solid, an aqueous solution, or a suspension. Typically, however, the at least one base is an aqueous solution. A base that is an aqueous solution can, for example, contain from about 40% to about 50% w/w alkali metal hydroxide. In general, at least a stoichiometric amount of base is utilized.

In one embodiment, about 1 to about 10 equivalents of the at least one base is used in effecting epoxidation.

In another embodiment, about 1 to about 3 equivalents of the at least one base is used in effecting epoxidation.

In yet another embodiment, about 1.1 to about 1.5 equivalents of the at least one base is used in effecting epoxidation.

Exemplary polar organic solvents that can be utilized in epoxidizing the formula (4) compound include, but are not limited to, for example, an aprotic polar organic solvent, such as, for example, acetone, methyl ethyl ketone, tetrahydrofuran, 1,4-dioxane, 1,3-dioxolane, 1,2-dimethoxyethane, diethylene glycol dimethyl ether, triethylene glycol dimethyl ether, tetraethylene glycol dimethyl ether, polyethylene glycol dimethyl ether, 1,2-diethoxyethane, diethylene glycol diethyl ether, triethylene glycol diethyl ether, tetra ethylene glycol diethyl ether, polyethylene glycol diethyl ether, acetonitrile, dimethylformamide, and dimethyl sulfoxide; a protic polar organic solvent, such as, for example, an alcohol, such as, for example, methanol, ethanol, n-propanol, isopropanol, n-butanol, sec-butanol, isobutanol, and tert-butanol; and combinations thereof.

In one embodiment, the organic solvent is an aprotic polar organic solvent.

In another embodiment, the protic polar organic solvent is isopropyl alcohol.

In one embodiment, the at least one solvent is a polar organic solvent and water and the polar organic solvent has a relatively high affinity for water.

In another embodiment, the at least one solvent is a polar organic solvent and water and the polar organic solvent has a high affinity for water In yet another embodiment, the at least one solvent is a polar organic solvent and water and the polar organic solvent is fully miscible with the water. An organic solvent is, for example, fully miscible with water when the solvent and water mixture formed upon mixing the solvent with the water is homogenous in appearance.

The ratio of the at least one polar organic solvent to water when using a polar organic solvent and water mixture may vary depending on such factors as, for example, the particular polar organic solvent used, strength of the at least one base, and the reaction temperature. A person of ordinary skill in the art, however, is generally familiar with routine experiments that can be used to easily and quickly determine the optimal polar organic solvent and water ratio.

In one embodiment, the ratio of the at least one polar organic solvent to water is less than about 10 by volume.

In another embodiment, the ratio of the at least one polar organic solvent to water is less than about 5 by volume.

In yet another embodiment, the ratio of the at least one polar organic solvent to water is less than about 2 by volume.

In an embodiment in which formula (4) compound is mixed with the at least one base after being extracted into the rich aqueous organic solvent light phase, the KF of the rich aqueous organic solvent light phase can be adjusted prior to being mixed with the at least one base. Adjusting the KF can, for example, keep salts and product in solution during the epoxidation reaction.

In one embodiment, the KF is adjusted to a range of from about 20 to about 35% w/v, based on the rich aqueous organic solvent light phase.

In another embodiment, the KF is adjusted to a range of from about 24% to about 26%, based on the rich aqueous organic solvent light phase.

In one embodiment, the KF is adjusted by adding water.

The formula (4) compound can be mixed with the at least one base in accordance with a batch, semi-continuous, or continuous process. In one embodiment, the formula (4) compound and the at least one base are mixed together in a continuous process, wherein a steady stream of formula (4) compound is added to a steady stream of the at least one base at a controlled rate so that about 1 to about 10, typically about 1 to about 3, and more typically about 1.1 to about 1.5 equivalents of the at least one base are added per mole of formula (4) compound.

The temperature at which the formula (4) compound can be contacted with the at least one base is not particularly restricted, but in general the temperature should be such that the reaction mixture does not solidify. For example, the temperature is typically about 50° C. or less, and more typically about 30° C. or less.

In crystallizing the formula (6) compound out of the reaction mixture, the reaction mixture and water are concurrently added together.

The reaction mixture and water can be added together in accordance with a batch, semi-continuous, or continuous process.

Optionally, the reaction mixture and water can be concurrently added to a seed crystal mixture containing at least one (2R,3S)-1,2-epoxy-3-(protected)amino-4-substituted butane seed crystal, water, and isopropyl alcohol. In one embodiment, the seed crystal mixture contains about a 3:1 ratio of water:isopropyl alcohol. In another embodiment, the at least one seed crystal has the same chemical formula as the formula (6) compound being crystallized out of the reaction mixture.

The amount of the at least one seed crystal utilized generally depends on a variety of factors, including, for example, the rate at which the reaction mixture and water are concurrently added together. Typically, however, the amount of at least one seed crystal used is at least about 1% by weight relative to the formula (6) compound being crystallized out of the reaction mixture.

Typically, the reaction mixture and water are concurrently added together at a temperature that allows crystallization to proceed.

In one embodiment, the reaction mixture and water are concurrently added together at a temperature of about 40° C. or less.

In another embodiment, the reaction mixture and water are concurrently added together at a temperature of about 20° C. or less.

In yet another embodiment, the reaction mixture and water are concurrently added together at a temperature of about 10° C. or less.

The temperature of the water typically ranges from about 0 to about 5° C.

Optionally, an in-line heat exchanger can be used to cool the reaction mixture before concurrently adding the reaction mixture and water together.

The reaction mixture and water can be concurrently added to a crystallizer optionally maintained at a temperature of about 0 to about 20° C., and typically at a temperature of about 0 to about 10° C.

As the reaction mixture and water are concurrently added together, a slurry comprising at least one formula (6) crystal is formed. Optionally, the resulting slurry comprising the at least one formula (6) crystal can be moderately agitated or stirred to produce formula (6) crystal(s) having satisfactory properties and uniform particle size. Optionally, the resulting slurry can be heated and/or cooled to improve the yield, quality, and characteristics of the formula (6) crystal(s).

In one embodiment, the slurry comprising at least one formula (6) crystal contains about a 3:1 ratio of water to the at least one solvent.

In another embodiment, the reaction mixture and water are added together in a continuous process, wherein a steady stream of reaction mixture is concurrently added to a steady stream of water at a controlled rate to produce the slurry comprising at least one formula (6) crystal and about a 3:1 ratio of water to the at least one solvent.

The at least one formula (6) crystal can be separated from the slurry through any ordinary solid-liquid separation technique, such as, for example, pressure filtration; filtration under reduced pressure; and centrifugation.

After being separated, the at least one formula (6) crystal can be washed with water and, if necessary, subsequently dried, for example, under atmospheric pressure, in, for example, a fluidized bed or vacuum.

EXAMPLES

The present invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth hereinbelow, but rather defined by the claims hereinbelow.

Example 1

Producing Mutagenized *Rhodococcus Erythropolis* Strain ATCC PTA-6648

The Mutagenized *R. erythropolis* strain ATCC PTA-6648 was produced by subjecting electrocompetent cells of *R. erythropolis* ATCC 4277 to an EZ::Tn™<R6Kyori/KAN-2>Tnp Transposome™ Kit purchased from Epicentre® Biotechnologies (Madison, Wis.).

The electrocompetent cells of *R. erythropolis* ATCC 4277 were produced in accordance with a modified version of the protocol set forth by R. van der Geize et al. in *Appl. Environ. Microbiol.* 66:2029-2036 (2000). First, 200 ml of alternative tryptic soy broth (ATSB) containing 1.8% soy protein, 0.2% yeast extract, 0.5% sodium chloride, 0.25% glucose, and 0.25% dipotassium phosphate was supplemented with 3.0% glycine. The broth was then inoculated with 4.0 ml of *R. erythropolis* ATCC 4277 overnight culture and shaken at 250 RPM at 30° C. until late-exponential phase (optical density at 600 nm=2-3). The cells of *R. erythropolis* ATCC 4277 were then pelleted by being centrifuged for 10 minutes at 4000× gravity at 4° C. and washed twice with cold distilled water. After centrifugation, the harvested cell pellet was resuspended in 2-3 ml of a 15% glycerol solution. 100 µl aliquots of the electrocompetent *R. erythropolis* ATCC 4277 cells were placed in 1.5 ml Eppendorf tubes and frozen at −80° C. until used.

Upon use, the frozen electrocompetent *R. erythropolis* ATCC 4277 cells were thawed on ice. Once thawed, one µl of EZ::TN™<R6Kyori/KAN-2>Tnp Transposome™ kit was added to the 1.5 ml Eppendorf tube and mixed with the cells. The resulting mixture was transferred to a 2-mm gapped cuvette, and subjected to electroporation. The electroporation was carried out on an Electro Cell Manipulator, Model ECM 630 (BTX Molecular Delivery Systems, Harvard Apparatus Inc., San Diego, Calif.). The field strength and resistance were set at 1.8 kV/cm and 400Ω (25 µF), respectively. One ml of TSB broth was added to the cuvette immediately following electroporation and the resulting cell suspension was transferred to a 14-ml Polypropylene Round-Bottom tube (Becton Dickinson Labware, Becton Dickinson and Company, Franklin Lakes, N.J.). The tube was shaken at 250 RPM at 30° C. for 4 hours. 100 µl aliquots of mutagenized *R. erythropolis* ATCC 4277 cells were then plated on TSB agar plates containing 250 µg/ml kanamycin. The plates were incubated at 30° C. for 3-4 days to allow colonies of mutagenized *R. erythropolis* ATCC 4277 cells to form.

The colonies of mutagenized *R. erythropolis* ATCC 4277 cells were picked by sterile toothpicks and placed into each 2 ml well of a 96-well plate, wherein each 2 ml well contained 400 µl TSB and 250 µg/ml kanamycin. The plate was then incubated in a Microtitertron Orbital Shaking Incubator (Appropriate Technical Resources, Inc., Laurel, Md.) for 48 hours at 700 RPM and 30° C. with relative humidity of 45%. 40 µl cell cultures were then taken from each well and inoculated into each 2 ml well of a fresh 96-well plate, wherein each 2 ml well contained 400 µl TSB and 250 µg/ml kanamycin. The newly inoculated plate was incubated in a Microtitertron Orbital Shaking Incubator (Appropriate Technical Resources, Inc., Laurel, Md.) for 24 hours at 700 RPM and 30° C. with relative humidity of 45%, and then centrifuged in an Eppendorf Centrifuge, Model 5810R (Brinkmann Instruments, Inc., Westbury, N.Y.) at 4000 rpm for 5 minutes. The supernatant was poured off by inverting the 96-well plates upside down for 30 seconds. The cells were then resuspended in 400 µl of an enzymatic reduction solution (pH 7.5) that contained 0.15% w/v of (S)-1-chloro-2-oxo-3-N-(tert-butoxycarbonyl)amino-4-phenylbutane substrate; 1.0% w/v glucose; and 0.1 M tricine buffer. The 96-well plate was again incubated in a Microtitertron Orbital Shaking Incubator (Appropriate Technical Resources, Inc., Laurel, Md.) for 24 hours at 700 RPM and 30° C. with relative humidity of 45% to enable the enzymatic ketone reduction of (3S)-1-chloro-2-oxo-3-N-(tert-butoxycarbonyl)amino-4-phenylbutane substrate to 1-chloro-2-hydroxy-3-N-(tert-butoxycarbonyl)amino-4-phenylbutane to occur in each 2 ml well. The content of each 2 ml well was then extracted into equal volumes of a 3:1 n-butanol:methanol mixture and analyzed by HPLC for bioconversion and diastereoisomeric purity. 2500 isolated colonies were screened in this manner.

When the content of each 2 ml well containing mutagenized *R. erythropolis* cultures was analyzed, about 90% of the 2500 isolates bioconverted about 100% of the (3S)-1-chloro-2-oxo-3-N-(tert-butoxycarbonyl)amino-4-phenylbutane substrate to 1-chloro-2-hydroxy-3-N-(tert-butoxycarbonyl)amino-4-phenylbutane, but only produced a d.e. of desired (2R,3S)-1-chloro-2-hydroxy-3-N-(tert-butoxycarbonyl)amino-4-phenylbutane compound of <92%. Only one isolate was found to have a d.e. in favor of desired (2R,3S)-1-chloro-2-hydroxy-3-N-(tert-butoxycarbonyl) amino-4-phenylbutane compound of >98%, and this isolate was deposited with the ATCC and assigned ATCC No. PTA-6648.

Examples 2 to 14

Preparing ATCC PTA-6648 Cells

The ATCC PTA-6648 culture of Example 1 was grown to a high cell density with a fed-batch fermentation process using a one stage seed culture to inoculate a fermentor vessel containing a complex batch medium. First, 100 ml seed medium (pH 7.2) containing 0.2% cerelose and 1% yeast extract was inoculated with 0.2 ml of ATCC PTA-6648 stock or overnight culture. Second, the inoculated seed medium was incubated and shaken in a Microtitertron Orbital Shaking Incubator (Appropriate Technical Resources, Inc., Laurel, Md.) for 22-26 hours at 250 RPM and 28° C. Third, a 5 liter B. Braun BioStat B fermentor (Sartorius BBI Systems, Inc. Bethlehem, Pa.) with 1.5 liter of a complex batch medium (pH 7.0-7.1) containing 0.3% yeast extract, 0.35% glycerol, 1.2% dipotassium phosphate, 0.17% citric acid, 0.13% sodium chloride, 0.18% magnesium sulfate, 0.046% ammonium sulfate, and 0.01% polypropylene glycol was inoculated with 75 ml of the inoculated seed medium. During fermentation, a concentrated feed medium containing 38% glycerol, 10% yeast extract, and 0.003% polypropylene glycol was employed to achieve high cell density while allowing the native intracellular expression of the ketoreductase enzyme. At about 70-72 hours, which is the point at which an optimal amount of ketoreducatase enzyme had accumulated, about 440 g/L of cells were harvested. The harvested cells were washed and diafiltrated with four-fold excess volume of water through a filtration membrane having a 0.2 µm pore size. The volume of the mixture containing the harvested ATCC PTA-6648 cells was subsequently reduced to produce a concentration of cells in the mixture of about 40% (w/v).

Biotransformation Reaction

A buffered aqueous system (pH 7.4) containing 28-32% (w/v) ATCC PTA-6648 cells was prepared by adding 0.1M sodium phosphate buffer, 2.2% (w/v) glucose, 6% (w/v) glycerol, and the mixture containing about 40% (w/v) ATCC PTA-6648 cells prepared above to a 5 liter B. Braun BioStat B fermentor. The agitation, temperature, pH, and air flow of the fermentor were monitored and controlled at 1200 RPM, 26° C., pH 7.4-7.6, and 1 vvm, respectively. The production of foam was limited by using PPG antifoam. The amounts of dissolved oxygen and $CO_2$ present in the buffered aqueous system were also monitored and maintained at $pO_2 \geq 30$.

The glucose and glycerol carbon sources were consumed by the ATCC PTA-6648 cells during biotransformation, and as a result were replenished as required to maintain a 2.2% (w/v) concentration of glucose and a 6% (w/v) concentration of glycerol. The glucose and glycerol were added to provide energy to the ATCC PTA-6648 cells.

A total of 6.0% (w/v) (S)-1-chloro-2-oxo-3-N-(tert-butoxycarbonyl)amino-4-phenylbutane substrate was added as a glycerol and water slurry to the buffered aqueous system (pH 7.4) containing about 28-32% (w/v) ATCC PTA-6648 cells as four separate 1.5% (w/v) (S)-1-chloro-2-oxo-3-N-(tert-butoxycarbonyl)amino-4-phenylbutane additions. The first addition was made at about 0 hours, the second at about 4 hours, the third at about 8 hours, and the last at about 23 hours. The biotransformation reaction was terminated at the times set forth in Table 1 hereinbelow.

In accordance with the biotransformation process, a total of 6% w/v (S)-1-chloro-2-oxo-3-N-(tert-butoxycarbonyl)amino-4-phenylbutane substrate was biotransformed in less than 72 hours to (2R,3S)-1-chloro-2-hydroxy-3-N-(tert-butoxycarbonyl)amino-4-phenylbutane with a % conversion >99.5%; a d.e. >95.5%, and a des-chloro impurity of ≦0.5 Area Percentage.

The results of the above outlined procedure are summarized in Table 1 set forth hereinbelow.

TABLE 1

Microbial Reduction Using ATCC PTA-6648

| | Fermentation Conditions | Biotransformation Conditions | | | | | | |
|---|---|---|---|---|---|---|---|---|
| Ex. Nos. | Time (hrs) | Time (hrs) | Substrate Loading (% w/v) | Cells (% w/v) | (2R,3S) d.e. (%) | % Biotransformed[1] | 2R,3S Diastereomeric Purity (%) | Des-Chloro. Impurity (Area %) |
| 2 | 84 | 24 | 4 | 30 | 95.9 | 99.7 | 98.0 | N/A[2] |
| 3 | 84 | 24 | 4 | 30 | 96.6 | 99.8 | 98.3 | N/A |
| 4 | 72 | 29 | 4 | 30 | 97.2 | >99.8 | 98.6 | 0.4 |
| 5 | 72 | 29 | 6 | 30 | 97.1 | >99.8 | 98.6 | 0.5 |
| 6 | 83 | 47 | 6 | 30 | 95.0 | 99.6 | 97.5 | N/A |
| 7 | 72 | 47 | 6 | 27 | 96.1 | 99.7 | 98.1 | 0.5 |
| 8 | 70 | 47 | 6 | 30 | 95.8 | 99.8 | 97.9 | 0.3 |
| 9 | 70 | 47 | 6 | 30 | 96.0 | 99.8 | 98.0 | 0.4 |
| 10 | 70 | 47 | 6 | 30 | 96.1 | 99.8 | 98.1 | 0.2 |
| 11 | 70 | 47 | 6 | 30 | 95.8 | 99.6 | 97.9 | 0.2 |
| 12 | 70 | 47 | 6 | 30 | 96.0 | 99.6 | 98.0 | 0.4 |
| 13 | 70 | 55 | 6 | 30 | 96.8 | 100 | 98.4 | 0.5 |
| 14 | 70 | 54 | 6 | 30 (+20% extra added) | 95.7 | 99.8 | 97.9 | 0.3 |

[1] % Biotransformed = Total chloroalcohols [(2R,3S)-1-chloro-2-hydroxy-3-N-(tert-butoxycarbonyl)amino-4-phenylbutane + (2S,3S)-1-chloro-2-hydroxy-3-N-(tert-butoxycarbonyl)amino-4-phenylbutane)]÷ Total chloroalcohols plus remaining (S)-1-chloro-2-oxo-3-N-(tert-butoxycarbonyl)amino-4-phenylbutane.
[2] "N/A" means "not applicable" and is used to indicate that the particular parameter was not measured.

Comparative Examples 15 to 22

Preparing *Rhodoccocus erythropolis* ATCC 4277 Cells

The ATCC 4277 cells were prepared in accordance with the process used in Example 2 to prepare ATCC PTA-6648 cells.

Biotransformation Reaction

A buffered aqueous system (pH 8.3) containing about 28-32% (w/v) *R. erythropolis* ATCC 4277 cells was prepared by adding 0.1M sodium phosphate buffer, 2.2% (w/v) glucose, 6% (w/v) glycerol, and the mixture containing about 40% (w/v) *R. erythropolis* ATCC 4277 cells prepared above to a 5 liter B. Braun BioStat B fermentor. The agitation, temperature, pH, and air flow of the fermentor were monitored and controlled at 1200 RPM, 26° C., pH 8.2-8.4, and 1 vvm, respectively. The production of foam was limited by using PPG antifoam. The amounts of dissolved oxygen present in the buffered aqueous system were also monitored.

The glucose and glycerol carbon sources were consumed by the *R. erythropolis* ATCC 4277 cells during biotransformation, and as a result were replenished as required to maintain a 2.2% (w/v) concentration of glucose and a 6% (w/v) concentration of glycerol. The glucose and glycerol were added to provide energy to the *Rhodococcus* cells.

The (S)-1-chloro-2-oxo-3-N-(tert-butoxycarbonyl)amino-4-phenylbutane substrate was added as a glycerol-water slurry in two equal portions at about 0 and about 4 hours. For Example, if using a 2% (w/v) total substrate loading, 1% (w/v) of the substrate is added at about 0 hours and 1% (w/v) of the substrate is added at about 4 hours.

The results of the above outlined procedure are summarized in Table 2 set forth hereinbelow.

TABLE 2

Microbial Reduction Using *R. erythropolis* ATCC 4277

| Ex. Nos. | Fermentation Conditions Time (hrs) | Biotransformation Conditions | | | | | 2R,3S Diastereomeric Purity (%) | Des-Chloro. Impurity (Area %) |
|---|---|---|---|---|---|---|---|---|
| | | Time (hrs) | Substrate Loading (% w/v) | Cells (% w/v) | d.e. (%) | % Biotransformed[1] | | |
| 15 | 72 | 44 | 4 | 30 | 90.6 | 44.8 | 95.3 | N/A[2] |
| 16 | 72 | 44 | 3 | 30 | 93.2 | 66.0 | 96.6 | N/A |
| 17 | 72 | 24 | 2 | 30 | 92.4 | 96.7 | 96.2 | N/A |
| 18 | 94 | 22 | 2 | 30 | 95.6 | 99.8 | 97.8 | N/A |
| 19 | 94 | 22 | 2.5 | 30 | 95.5 | 99.8 | 97.8 | N/A |
| 20 | 94 | 22 | 3 | 30 | 94.6 | 99.7 | 97.3 | N/A |
| 21 | 96 | 22 | 2 | 30 | 96.1 | 99.5 | 98.1 | 2.2 |
| 22 | 96 | 22 | 2 | 30 | 96.4 | 99.7 | 98.2 | 2.1 |

[1] % Biotransformed = Total chloroalcohols [(2R,3S)-1-chloro-2-hydroxy-3-N-(tert-butoxycarbonyl)amino-4-phenylbutane + (2S,3S)-1-chloro-2-hydroxy-3-N-(tert-butoxycarbonyl)amino-4-phenylbutane)] ÷ Total chloroalcohols plus remaining (S)-1-chloro-2-oxo-3-N-(tert-butoxycarbonyl)amino-4-phenylbutane.
[2] "N/A" means "not applicable" and is used to indicate that the particular parameter was not measured.

Example 23

Each resulting post-biotransformation slurry of examples 2, 3, 5, 6, 10, 11, and 14 was then centrifuged to produce 1) a heavy layer containing mostly (2R,3S)-1-chloro-2-hydroxy-3-N-(tert-butoxycarbonyl)amino-4-phenylbutane crystals and 2) a supernatant containing mostly undesired impurities, such as, for example, propylene glycol; salts; (2S,3S)-1-chloro-2-hydroxy-3-N-(tert-butoxycarbonyl)amino-4-phenylbutane; and >70% of the ATCC PTA-6648 cells.

In producing the heavy layer, the post-biotransformation slurry of each of the examples 2, 3, 5, 6, 10, 11, and 14 was first chilled to 1-5° C. (taking care not to freeze the slurry) and then agitated for 10 minutes. Each chilled slurry was then split into two equal portions, and each portion was added to a separate 750 ml centrifuge bottle. Both portions were then centrifuged in a Beckman Coulter Allegra® 64R High-Speed Refrigerated Benchtop Centrifuge (Beckman Coulter, Inc., Fullerton, Calif.) at 3700 rpm for 5 minutes. The heavy layer of each portion was harvested and the supernatant containing all of the various impurities discarded.

In batch centrifugations, the size of the centrifuge bottle, volume of the slurry, temperature of the slurry, rpm of the centrifuge, and length of time centrifuged can all affect the portion of undesired cells contained in the heavy layer, and therefore the amount of impurities removed via the supernatant. The portion of undesired cells contained in the heavy layer can also affect the water content of the isopropyl alcohol (IPA KF), which can lead to a further decrease in the amount of impurities removed via the supernatant.

Each harvested heavy layer was dewatered by being centrifuged in a Beckman Coulter Allegra® 64R High-Speed Refrigerated Benchtop Centrifuge (Beckman Coulter, Inc., Fullerton, Calif.) at 3700 rpm for 25 minutes. The resulting aqueous supernatant (~20 ml) was decanted, and each of the drier heavy layers examined.

Upon being examined, each of the drier heavy layers was found to contain a dark colored top layer and a light colored bottom layer. The dark colored top layer typically contained mostly ATCC PTA-6648 cells and <1% by weight, based on the drier heavy layer, of (2R,3S)-1-chloro-2-hydroxy-3-N-(tert-butoxycarbonyl)amino-4-phenylbutane. The light colored bottom layer typically contained mostly (2R,3S)-1-chloro-2-hydroxy-3-N-(tert-butoxycarbonyl)amino-4-phenylbutane; water; and residual amounts of ATCC PTA-6648 cells. The dark colored top layers were manually removed from the drier heavy layers with a spatula. The dark colored top layers were combined and assayed for (2R,3S)-1-chloro-2-hydroxy-3-N-(tert-butoxycarbonyl)amino-4-phenylbutane, the results of which are set forth hereinbelow in Table 3 in the column titled "Dark Colored Top Layer (2R,3S) d.e. %".

The light colored bottom layer of each of the heavy layers was added along with 420 ml Isopropyl alcohol (IPA) to a single beaker. The contents of the beaker were stirred at 25° C. for 15 minutes to produce a bottom layer/IPA slurry.

50 ml IPA was then mixed with 7.2 g Darco® KB carbon (American Norit Co., Inc., Atlanta, Ga.) in a beaker to produce a carbon/IPA slurry. The carbon/IPA slurry was then added to the bottom layer/IPA slurry. The resulting bottom layer/carbon/IPA slurry was rinsed with 10 ml IPA.

The rinsed bottom layer/carbon/IPA slurry was stirred for at least 30 minutes at 25° C. and then centrifuged in a Beckman Coulter Allegra® 64R High-Speed Refrigerated Benchtop Centrifuge (Beckman Coulter, Inc., Fullerton, Calif.) at 3700 rpm for 15 minutes. The subsequent slurry was decanted to separate a first heavy phase containing mostly carbon and ATCC PTA-6648 cells from a first rich aqueous IPA light phase containing mostly (2R,3S)-1-chloro-2-hydroxy-3-N-(tert-butoxycarbonyl)amino-4-phenylbutane; water; and residual amounts of ATCC PTA-6648 cells. The water content of the first rich aqueous IPA light phase (IPA KF) was 15-20%.

The first heavy phase was added along with 120 ml IPA to a beaker. The contents of the beaker were stirred for at least 30 minutes at 25° C. to produce a slurry. The slurry was centrifuged in a Beckman Coulter Allegra® 64R High-Speed Refrigerated Benchtop Centrifuge (Beckman Coulter, Inc., Fullerton, Calif.) at 3700 rpm for 15 minutes. The centrifuged slurry was decanted to separate a second heavy phase containing mostly carbon and ATCC PTA-6648 cells from a second rich aqueous IPA light phase containing mostly (2R, 3S)-1-chloro-2-hydroxy-3-N-(tert-butoxycarbonyl)amino- 4-phenylbutane; water; and residual amounts of ATCC PTA-6648 cells. The IPA KF of the second rich aqueous IPA light phase was about 5-9%.

The two rich aqueous IPA light phases were combined into a single rich aqueous IPA light phase stream and polish filtered across a 0.45 micron filter, which was subsequently washed with a minimal amount of IPA. The IPA KF of the resulting rich aqueous IPA light phase stream was adjusted to 25% by adding water. The rich aqueous IPA light phase stream was assayed for (2R,3S)-1-chloro-2-hydroxy-3-N-(tert-butoxycarbonyl)amino-4-phenylbutane, the results of which are set forth hereinbelow in Table 3 in the column titled "Combined IPA Light Phase (2R,3S) d.e. %".

The second heavy phase was assayed for (2R,3S)-1-chloro-2-hydroxy-3-N-(tert-butoxycarbonyl)amino-4-phenylbutane, the results of which are set forth hereinbelow in Table 3 in the column titled "Residual Heavy Phase (2R,3S) d.e. %".

It is of import to note that although at laboratory scale the harvested heavy layer was dried via a centrifugation dewatering step, at plant scale the dewatering centrifugation step can be eliminated by centrifuging the post-biotransformation slurry in a Westfalia Concurrent Extractor-Decanter (Westfalia Separator AG, Oelde, Germany) to directly produce a sufficiently dry heavy layer. Additionally, although laboratory scale requires the top and bottom layers of the dried heavy layer to be manually separated, at plant scale the manual separation step is eliminated by simply selecting the appropriate ring dam and optimizing the differential speed between the scroll and bowl of the Westfalia Extractor-Decanter (Westfalia Separator AG, Oelde, Germany). That is, the (2R,3S)-1-chloro-2-hydroxy-3-N-(tert-butoxycarbonyl)amino-4-phenylbutane solids can be directly separated from the ATCC PTA-6648 cells by properly adjusting the settings of the Westfalia Extractor-Decanter (Westfalia Separator AG, Oelde, Germany).

The resulting effect of the above centrifugation process on the d.e. of the desired (2R,3S)-1-chloro-2-hydroxy-3-N-(tert-butoxycarbonyl)amino-4-phenylbutane diastereomer is set forth hereinbelow in Table 3.

warming the (2R,3S)-1-chloro-2-hydroxy-3-N-(tert-butoxycarbonyl)amino-4-phenylbutane rich IPA stream of Example 19 to 30° C., and then combining the warmed stream with 1.5 eq. (relative to the (2R,3S)-1-chloro-2-hydroxy-3-N-(tert-butoxycarbonyl)amino-4-phenylbutane activity) of 45% w/w KOH/water solution to form a (2R,3S)-1,2-epoxy-3-N-(tert-butoxycarbonyl)amino-4-substituted butane containing reaction mixture. The epoxide containing reaction mixture was stirred vigorously at 30° C. for 5 minutes and then immediately cooled to 5° C. The reaction mixture was subsequently assayed for (2R,3S)-1,2-epoxy-3-N-(tert-butoxycarbonyl)amino-4-phenylbutane, the results of which are set forth hereinbelow in Table 4.

Crystallizing out (2R,3S)-1,2-epoxy-3-N-(tert-butoxycarbonyl)amino-4-phenylbutane 400 mg of (2R,3S)-1,2-epoxy-3-N-(tert-butoxycarbonyl)amino-4-phenylbutane seed crystals were placed in a 3 L 3 neck round bottomed flask and a mixture containing 6 ml water and 2 ml IPA was added to the flask to form a seed crystal/water/IPA slurry. The slurry was chilled to 0-5° C. and, while vigorously being agitated, a 3:1 ratio of cold 1-5° C. water antisolvent and epoxide containing reaction mixture were concurrently added to the seed crystal containing flask so as to cause the (2R,3S)-1,2-epoxy-3-N-(tert-butoxycarbonyl)amino-4-phenylbutane to crystallize out of the epoxide containing reaction mixture. That is, the (2R,3S)-1,2-epoxy-3-N-(tert-butoxycarbonyl)amino-4-phenylbutane crystallized out of the epoxide containing reaction mixture by concurrently adding water and the epoxide containing reaction mixture to the flask containing the seed crystal at such a rate that the resulting slurry comprising (2R,3S)-1,2-epoxy-3-N-(tert-butoxycarbonyl)amino-4-phenylbutane crystals contained a ratio of water to IPA of about 3:1. After all of the epoxide containing reaction mixture was added, the slurry was cooled to 0-5° C. and mildly agitated for 3 hours. The slurry was then filtered across a 24 cm #604 filter paper and the (2R,3S)-1,2-epoxy-3-N-(tert-butoxycarbonyl)amino-4-phenylbutane cake was washed with 360 ml 1-5° C. water. The (2R,3S)-1,2-epoxy-3-N-(tert-butoxycarbonyl)amino-4-

TABLE 3

Using IPA Centrifugation to Improve the D.E. of (2R,3S)-1-chloro-2-hydroxy-3-N-(tert-butoxycarbonyl)amino-4-phenylbutane

| Ex. Nos. | Post-bioconversion (2R,3S) d.e. (%) | Combined IPA Light Phase (2R,3S) d.e. (%) | % Increase in (2R,3S) d.e.[1] | Supernatant (2R,3S) d.e. (%) | Dark Colored Top Layer (2R,3S) d.e. (%) | Residual Heavy Phase (2R,3S) d.e. (%) |
|---|---|---|---|---|---|---|
| 2 | 95.9 | 99.0 | 3.1 | 17.9 | N/A[2] | 98.8 |
| 3 | 96.6 | 99.0 | 2.4 | 23.6 | N/A | 98.4 |
| 5 | 97.1 | 99.1 | 2.0 | 2.3 | 86.7 | 99.1 |
| 6 | 95.0 | 96.8 | 1.8 | 32.5 | Na | 95.7 |
| 10 | 96.1 | 97.5 | 1.4 | 29.0 | 58.3 | 97.4 |
| 11 | 95.8 | 96.7 | 0.9 | 14.3 | 55.6 | 96.3 |
| 14 | 95.7 | 97.6 | 1.9 | 13.4 | 56.9 | 97.3 |

[1]"% increase in (2R,3S) d.e" = "Combined IPA Light Phase (2R,3S) d.e. (%)" − "Post-bioconversion (2R,3S) d.e (%)".
[2]"N/A" means "not applicable" and is used to indicate that the particular parameter was not measured.

Example 24

Epoxidation Reaction (2R,3S)-1-chloro-2-hydroxy-3-N-(tert-butoxycarbonyl)amino-4-phenylbutane was converted to (2R,3S)-1,2-epoxy-3-N-(tert-butoxycarbonyl)amino-4-phenylbutane by first phenylbutane epoxide crystals were dried under vacuum with a nitrogen sweep at 25-30° C. until a constant weight was obtained.

The entire process from biotransformation to epoxidation yielded 80.5 M % of (2R,3S)-1,2-epoxy-3-N-(tert-butoxycarbonyl)amino-4-phenylbutane.

TABLE 4

Epoxidation of
(2R,3S)-1-chloro-2-hydroxy-3-N-(tert-butoxycarbonyl)amino-4-phenylbutane
to (2R,3S)-1,2-epoxy-3-N-(tert-butoxycarbonyl)amino-4-phenylbutane

| Ex. Nos. | M % Yield of (2R,3S) Epoxide Crystals | Epoxide Assay (2R,3S) d.e. (%) | Post-Centrifugation (2R,3S)-1-chloro-2-hydroxy-3-N-(tert-butoxycarbonyl)amino-4-phenylbutane d.e. (%) | Post-epoxidation Des-Chloro. Impurity (Area %) |
|---|---|---|---|---|
| 10 | 80.5 | 97.4 | 97.5 | 0.19% |
| 14(A) | 78.4 | 97.7 | 97.6 | 0.15% |
| 14(B) | 78.2 | 97.6 | 97.6 | 0.15% |

What is claimed is:

1. A mutagenized *Rhodococcus erythropolis* having ATCC deposit no. PTA-6648.

* * * * *